United States Patent [19]

Devine

[11] Patent Number: 4,517,053
[45] Date of Patent: May 14, 1985

[54] APPARATUS FOR SAMPLING PAPER PULP LIQUOR

[76] Inventor: James B. Devine, 505 S. Wilbur, Walla Walla, Wash. 99362

[21] Appl. No.: 440,093

[22] Filed: Nov. 8, 1982

[51] Int. Cl.³ .............................................. D21C 7/12
[52] U.S. Cl. ................................ 162/251; 73/863.23; 73/863.81; 162/238; 162/263; 422/62; 422/119
[58] Field of Search ............ 73/863.23, 863.24, 863.81; 162/49, 198, 263, 62, 251, 238, 252; 422/119, 62

[56] References Cited

U.S. PATENT DOCUMENTS

| | | | |
|---|---|---|---|
| 1,860,836 | 5/1932 | Gustin | 162/251 |
| 2,746,297 | 5/1956 | Martin | 73/863.24 |
| 3,250,128 | 5/1966 | Cassel | 73/863.23 |
| 4,065,348 | 12/1977 | Zimmerman | 162/49 |
| 4,192,708 | 3/1980 | Bergstrom et al. | 162/49 |

FOREIGN PATENT DOCUMENTS

| | | | |
|---|---|---|---|
| 0124201 | 1/1959 | U.S.S.R. | 73/862.24 |
| 0607127 | 5/1978 | U.S.S.R. | 73/863.24 |

Primary Examiner—Steve Alvo
Attorney, Agent, or Firm—Keith S. Bergman

[57] ABSTRACT

In a paper making process the liquid fraction of wood pulp stock liquor is sampled between the bleaching and caustic extraction stages and after caustic introduction to regulate the amount of caustic introduced into the pulp stock liquor. A particular sampling device with a lower pressure chamber extracts that stock liquor from the periphery of a higher pressure pipe and passes the sample to previously known continuous testing apparatus. A particular double screen type interfacing joins the sampling device and pulp stock to allow liquor extraction without excessive wear or plugging of the interface.

1 Claim, 6 Drawing Figures

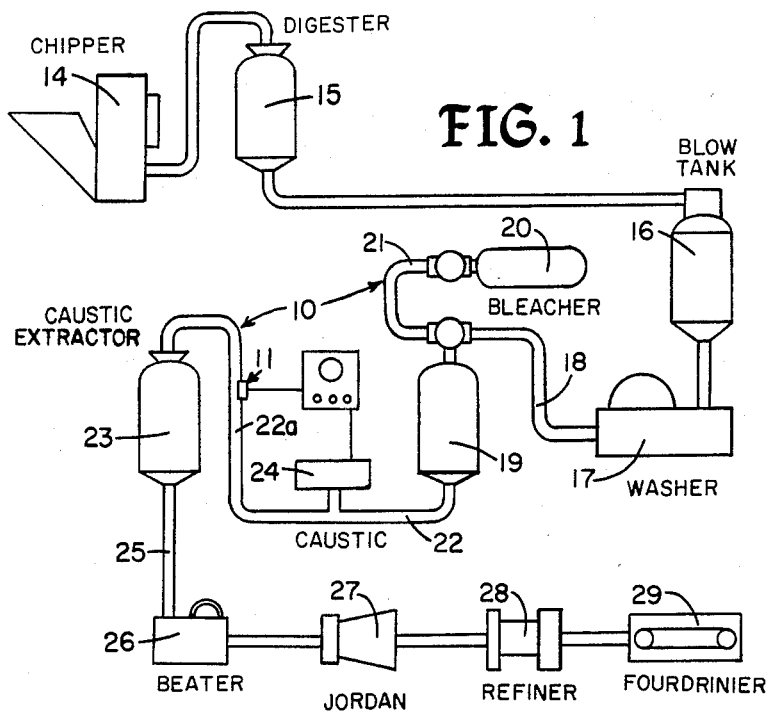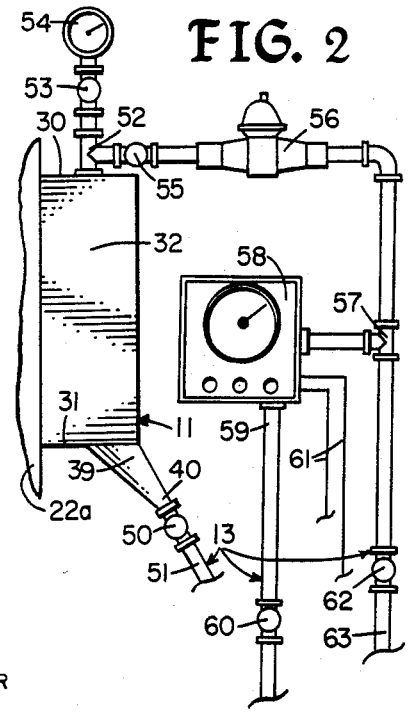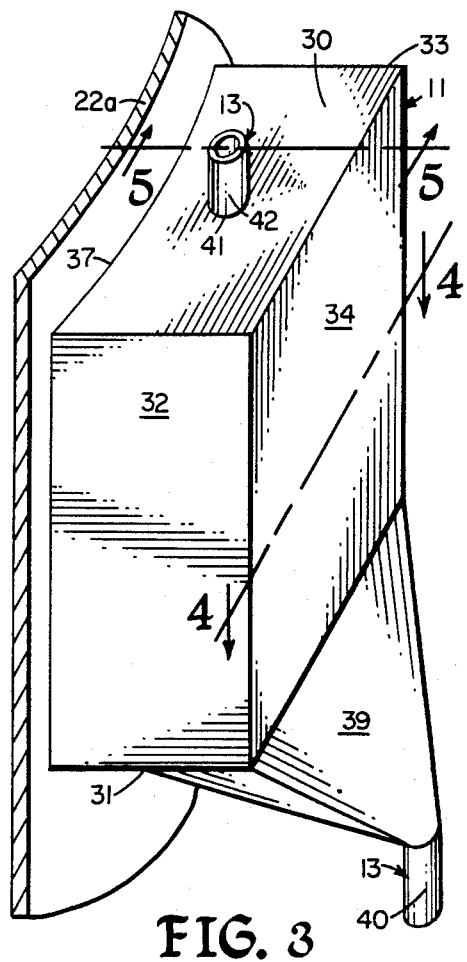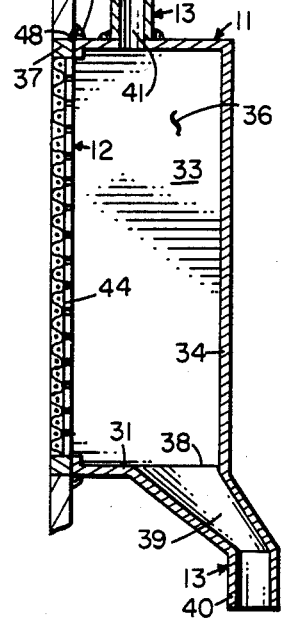

APPARATUS FOR SAMPLING PAPER PULP LIQUOR

BACKGROUND OF THE INVENTION

Related Applications

There are no applications related hereto heretofore filed in this or any foreign country.

Field of Invention

My invention relates generally to a process for sampling pulp stock liquor after caustic introduction and between a bleacher and a subsequent caustic extractor and to apparatus for such sampling that extracts a peripheral sample from a pressurized transit pipe without excessive wear or plugging.

Description of Prior Art

In modern day practice of making paper from wood fibers, after an aqueous based pulp is formed from the wood fibers, whether by chemical or mechanical means or a combination of both, the pulp is commonly bleached in one fashion or another to render the ultimate paper product to be formed whiter and brighter and more stable to light. Commonly this bleaching process is of a compound nature with multiple stages of bleaching by chlorination and subsequent caustic extraction, commonly by caustic soda. It is with this process that my invention is concerned.

Heretofore bleaching commonly has been carried out in a vat, the bleached pulp then transferred through pipes in which caustic soda was added to the mixture, and the mixture then transferred to an extractor vat where caustic extraction was completed. After the causticized pulp left the caustic extractor it was sampled to attempt to regulate the amount of caustic soda that had been introduced into the mixture. The transfer piping between bleacher and caustic extractor and the caustic extractor itself contained substantial volumes of pulp stock and the passage of this stock through this apparatus was relatively slow, so in sampling the mixture after its exit from the caustic extractor there would be a substantial lag of oftentimes twenty-four hours or more between the time that caustic was introduced and the time of measurement of the amount of that caustic. This has proven to be a relatively inaccurate method of regulating the amount of caustic introduced and has resulted in the process not having any fine control which oftentimes has been wasteful of caustic and productive of inferior product.

My process alleviates this problem by changing the point of sampling of the pulp liquor to a point in the transfer piping between the bleacher and caustic extractor, downstream from the point of caustic introduction. This allows a much finer and much more rapid regulation of caustic content in the mixture than may be had by the heretofore existing sampling method. In compound, multi-stage processes involving several belaching and caustic extraction stages, which are common in present day paper making, the same type of measurements may be had in each of the several stages.

In sampling pulp stock for caustic content it is generally desirable to separate the fiberous and liquid portions of the stock and thereafter determine caustic content of the liquid fraction by means of a continuous flow-through Ph meter. This sampling in the present day paper making art is generally accomplished by extracting liquor from the medial portion of a transfer pipe by means of an elongate probe extending from the exterior of the pipe inwardly to a medial position. This means of sampling has not proven too satisfactory in several aspects. The pulp stock is fairly abrasive and necessarily moving relative to a probe so that it causes substantial abrasion which oftentimes limits probe life to short periods of a few days or so. Again, the pulp stock must, of necessity, be maintained under at least some pressure in a transfer pipe to accomplish its transfer. It has been found that fairly substantial pressures are desirable and these pressures oftentimes make it most difficult and time consuming, if not impossible, to remove and replace probes during operation with pressurized pulp. Such probes also have tended to plug readily with fiberous material and to produce inaccurate or inconsistent samplings because of their position in a transfer pipe and because of the nature of the fluid flow in the pipe and about the probe. My invention alleviates these problems by providing a new and novel sampler that samples the liquid fraction of pulp liquor at the periphery of a transfer pipe.

I provide a sampling device that has a porous type interface configuratively compatible with the exterior surface of the transfer pipe from which a sample is to be extracted. This geometry allows pulp in the pipe to move in its normal fashion without sampler introduced turbulence so that the moving pulp tends to clean the pipe-facing surface of the interface to aid in preventing it clogging. The interface itself is formed of two adjacent porous elements, each having openings dissimilarly arrayed, which tends to prevent clogging by distributing pressure differentials relatively evenly on the entire surface of the interface rather than creating small areas of substantial pressure difference as would be done with the single porous membrane. A collection chamber adjacent the porous interface provides means for regulation of pressure differentials between the transfer pipe and the ambient atmosphere so that a pressure differential may be maintained at the interface low enough to aid in preventing plugging. My invention is generally positioned on a substantially vertically oriented transfer pipe so that the pipe position tends to aid homogeneous mixing of the pulp to aid the consistency and reproducability of samples obtained by use of the device.

My invention in my sampling device resides not in any single enumerated element or function per se but rather in the combination of all of the elements and functions for the purposes specified and it is distinguished from the prior art primarily in this fashion.

SUMMARY OF THE INVENTION

My invention generally provides a sampling device for continuously sampling the liquid fraction of pulp stock in a vertical transfer pipe between a bleacher and a caustic extractor in the paper making process.

A peripherally defined extraction chamber provides one surface that is permeable to the liquid fraction but not for the fiberous fraction of pulp stock. This permeable surface is particularly configured to be geometrically compatible and co-extensive with the inner surface of the transfer pipe through which pulp stock is transferred. The permeable surface of the extraction chamber is formed by two adjacent porous elements each having pores uniformly arrayed but not generally coincident, such as a screen and a plate with holes in it. The extraction chamber is provided with a pressure regulating valve so that the pressure therein may be variably regulated between higher pipe pressure and lower atmospheric pressure. Conduit means communicate from the extraction chamber to measuring devices and additional conduit means allow flushing and wastage of samples. My sampling device is physically attached to the peripheral surface of a vertical transfer pipe from which a sample is to be extracted.

In creating such a device it is:

A principal object of my invention to provide a sampler to extract a sample of the fluid fraction of paper pulp in a continuous fashion from the periphery of a pressurized transfer pipe without materially disrupting the flow of pulp in that pipe.

A further object of my invention to provide such a sampling device that has an interface surface geometrically compatible with the interior surface of the transfer pipe carrying it, with no elements extending into the interior of that pipe.

A further object of my invention to provide such an interface that is formed of two adjacent permeable elements, each having arrayed holes that are not generally coincident.

A further object of my invention to provide such a sampling device that has an extraction chamber adjacent the permeable element with means of adjustably regulating the pressure therein between that of the transfer pipe and that of the ambient atmosphere.

A further object of my invention to provide such a sampling device that is positioned between a bleacher and a caustic extractor after introduction of caustic into pulp in the transfer pipe so that the amount of caustic introduced may be finely monitored and controlled.

A still further object of my invention to provide such a device that is of new and novel design, of rugged and durable nature, of simple and economic manufacture and one otherwise well suited to the uses and purposes for which it is intended.

Other and further objects of my invention will appear from the following specification, claims and accompanying drawings which form a part hereof. In carrying out the objects of my invention, however, it is to be understood that its essential features are susceptible of change in design and structural arrangement with only one preferred and practical embodiment being illustrated as is required.

BRIEF DESCRIPTION OF DRAWINGS

In the accompanying drawings which form a part hereof and wherein like numbers of reference refer to similar parts throughout:

FIG. 1 is a diagrammatic flow diagram of a typical, somewhat simplified, paper making process showing the location of my invention therein and its relationship thereto.

FIG. 2 is a partial view showing my invention and its immediately associated structures and circuitry.

FIG. 3 is an isometric, surface view of my sampling device in place on a portion of a transfer pipe.

FIG. 4 is an orthographic, horizontal, cross-sectional view of the sampling device of FIG. 3, taken on a line 4—4 thereon in the direction indiated by the arrows.

FIG. 5 is an orthographic, vertical, cross-sectional view of the device of FIG. 1, taken on the line 5—5 thereon in the direction indicated by the arrows.

FIG. 6 is a somewhat enlarged, partial, cut-away view of the permeable element of my sampling device showing its two porous elements.

DESCRIPTION OF THE PREFERRED EMBODIMENT

My invention generally comprises sampler 11 having permeable interface element 12 communicating with a transfer pipe carrying pulp stock, at a point between the beaching and caustic extraction state 10, to extract the liquid fraction therefrom and pass that sample continuously through sample circuitry 13 to allow measurement of caustic content.

A simplified paper making process common in the present day art is illustrated diagrammatically, in its essence at least, in FIG. 1. In the making of wood fiber paper the clean wood is particulated in some fashion or other, in the instance shown by mechanical chipping in chipper 14 and in other instances by grinding, chemical action or similar processes. The particulated wood is passed, generally admixed with water, to digester 15 where the cellulose fibers are more or less separated from the liquid by various mechanical and chemical processes commonly involving heating in an acid bi-sulfide, caustic soda or sulfide solution. The mixture then commonly known as 'crude pulp' is passed to blow tank 16 for further fiber separation and liqnin removal. After this pulping operation the unbleached pulp or so-called 'brown stock' is washed to free it of soluable impurities and screened to remove particulate matter such as knots, dirt and unpulped fiber bundles. The brown stock may be used at this point to make paper but commonly it is too crude to make many desired paper products as it contains impurities that impart color to the products formed therefrom. Commonly this brown stock is bleached to remove the coloring products, change them to colorless products and increase the heat and light stability of paper formed from the pulp. This bleaching is commonly chemically accomplished by chlorine, hypochlorite, chlorine dioxide and sometimes peroxides, hydrosulfites and chlorohydrides.

In the current state of the paper making art this bleaching is generally accomplished in a compound multi-stage process, commonly involving plural stages of bleaching with subsequent caustic extraction. A typical multi-stage bleaching operation for a high brightness sulfite pulp comprises (1) chlorination, (2) caustic soda extraction, (3) addition of chlorine dioxide, (4) caustic soda extraction and (5) another treatment by chlorine dioxide with interstage washing with water to remove soluble products formed during the bleaching and extraction stages. In the process illustrated only a single bleaching and caustic extraction stage 10 is shown for convenience of illustration and description.

In this bleaching stage illustrated brown stock passes through conduit 18 to bleacher 19 which is supplied with bleach from container 20 through conduit 21. The bleached product passes from the bleacher through conduit 22 to caustic extractor 23. Commonly conduit 22 exits from the bottom of normally vertical bleacher 19, follows a horizontal course for some distance and then rises vertically in portion 22a to enter the upper part of caustic extractor 23. Caustic is introduced from caustic source 24, commonly in the horizontal portion of conduit 22, and tends to mix with the pulp stock during its course of transit to the caustic extractor. My sampler 11 is positioned to extract liquid samples from vertical portion 22a of conduit 22 and allow measurement of the caustic content in the sample to use that information to regulate the amount of caustic introduced.

If multi-stage bleaching is used in a paper making process, one or more additional bleaching and caustic extraction stages 10 would be added to the process, in series, after the pulp passes through caustic extractor 23 and they would be serviced in the same way as the bleaching and extraction stage illustrated.

After the bleached pulp stock leaves the final caustic extractor it passes through conduit 25 to beater 26, thence to Jordan 27 and refiner 28 to ultimately be reduced to paper stock in Fourdrinier 29.

Heretofore the measurement of caustic content in the pulp stock has generally been accomplished in conduit 25 after the stock has completed the bleaching and caustic extraction processes. Since in the common paper processes this bleaching and extraction takes some substantial period of time and involves substantial volumes of pulp stock there has been a lengthy delay in sensing the amount of contained caustic in the bleached stock. Because of this bleaching and extraction processes have not been too finely controllable and this has produced inferior products and wasted substantial amounts of chemicals.

My sampler 11 provides a peripherally defined body comprising similar top 30 and bottom 31, similar sides 32, 33, planar back 34 and permeable element 12 all communicating at adjacent edges to define sample chamber 36. These elements are peripherally configured substantially as illustrated in FIG. 3 and their adjacent edges are mechanically joined to form a rigid, box-like structure with the permeable element 12 forming an interface between the sampler and the channel defined by conduit 22a. Normally my sampler will have a back of some few inches in each dimension, about four inches by six inches. Conduit 22a will normally be formed as a cylinder commonly of twenty-four or more inches in diameter and the conduit-facing element of my sampler will be appropriately configured in curvilinear form similar to the pipe. The sampler 11 is positioned in hole 37 in conduit 22a so that outer surface of permeable perforated element 12 conforms to the configuration of the inner surface of conduit 22a, as illustrated.

The exact size of my sampler is not too critical but generally if it be too small it may not withdraw an appropriate amount of fluid from the pulp stock pipe and if it be too large it may be difficult to regulate the pressure differential between pulp stock carried in conduit 22 and the extraction chamber of the sampler, and in either event plugging of permeable element 12 may occur. I prefer a permeable element having an area of about twenty-four square inches, preferably arrayed as a rectangle with its smaller dimension being not less than half of its larger dimension and the longer dimension being oriented in the direction of pulp stock flow.

Bottom 31 may drain through depending sump 38 to exhaust pipe 39 to provide a gravity activated means of wasting fluid from sampling chamber 35 if desired. Top 30 defines sampling hole 40 which carries sampling pipe nipple 41 in mechanical joinder with the upper surface of the top thereabout.

Permeable perforated element 12 is illustrated especially in FIG. 6 and in the cross-sectional view of FIGS. 4 and 5. The element is formed with outer screen 41 and inner perforated plate 44, each defining respectively holes 45 and 46 which by reason of different size and spacing are not generally coincident with each other. These elements are joined at their edges by rigid peripheral frame 47 and the whole structure is formed as a rolled surface as specified and illustrated so that the outer surface of screen 43 may be coincident with the inner surface of conduit 22a. The periphery of frame 47 is substantially the same size and configuration as the adjacent edges of the sampler body so that the frame and body may be mechanically joined. The combined thickness of screen 43 and plate 44 is preferably substantially the same as the thickness of peripheral frame 47 and this thickness is also preferably substantially the same as that of conduit 22a so that there is a common linear joint 48 between all three members which may be welded by weld 49 to form a gas tight seal between all elements and the ambient atmosphere.

Holes 45, 46 in screen 43 and plate 44 may vary in both size and number, through certain limits, while still fulfilling the purposes of my invention. In general, however, the total area of all holes in screen 43 should be half or more of the area of the screen and the total area of all holes 46 in plage 44 should be something less than half of the area of that plate. In addition the holes should be uniformly arrayed but in different fashion in the two elements so that relatively few holes in either element are completely coincident with holes in the other element. Generally the total area of holes in plate 44 should be in the range of thirty percent of total plate area though the device is operative, depending on various parameters, through quite a range of hole sizing and array. The reason for keeping coincident holes in the two permeable elements at a minimum is to provide a more even distribution of pressure differentials on the pipe facing surface of the screen to aid in preventing clogging of that screen by the fiberous faction of the pulp stock.

The ancillary conduit structure associated with my sampler is shown especially in the illustration of FIG. 2. Exhaust pipe 40 communicates to normally closed valve 50 and thence through conduit 51 to waste any material exhausted through this conduit. Sampling nipple 42 communicates with 'T' joint 52, the first arm of which carries normally open shut-off valve 53 and thence communicates to pressure gauge 54; the second arm communicates through normally open valve 55 to variable pressue adjustment valve 56 and thence to 'T' joint 57. The first arm of the 'T' joint 57 communicates to continuous Ph measuring device 58 having exhaust conduit 59 controlled by exhaust valve 60 and providing control signals through electrical circuitry 61. The second arm 'T' joint 57 communicates through normally closed valve 62 to exhaust conduit 63 to waste material passing therethrough and provide a backflush circuit.

Having thusly described the structure of my invention, its operation may be readily understood.

Firstly the sampler, as specified and described, is constructed and established in conduit 22a between bleacher 19 and caustic extractor 23, downstream of caustic source 24. The actual position of the sampler is preferably on vertically oriented portion 22a of the conduit some distance downstream from caustic source 24 so that the caustic in the conduit may be reasonably homogeneously admixed at the point of sampling. The sampler is installed in hole 37 in the conduit with the conduit-facing surface of screen 43 substantially coincident with the original inner surface of the conduit. The sampler is structurally joined to the conduit by welding along the line of joinder of the elements.

The ancillary structure described and illustrated in FIG. 2 are established as specified and the sampler is then in operative condition. Ph meter 58 is of a continuous flow-through type heretofore known and commonly used by the paper industry to determine caustic content of pulp stock. Such devices commonly translate the amount of contained caustic into an electrical signal that passes through electrical control circuitry 61 to regulate caustic imput to a predetermined value by methods and with apparatus not shown but heretofore well known in the paper making art.

To use my sampler, exhaust valve 50 is closed and valves 53 and 54 are opened. Variable pressure regulating valve 56 is then adjusted to create a relative pressure in sampling chamber 35 somewhat less than the pressure of pulp stock in conduit 22a. Normally the pulp stock in conduit 22a will be moved under pressure substantially above that of the ambient atmosphere. The pressure differential between that of the conduit and the sampling chamber normally will be some few pounds but, again, may vary through a limited range and must be adjusted in individual cases to meet the requirements of the particular parameters to allow extraction of the liquid fraction of the pulp stock and yet prevent clogging of permeable element 12. Normally this pressure requirement will vary in the range of a three to six pound per square inch differential.

When the sampler is adjusted to this condition and so maintained fluid will be separated from the pulp stock in the conduit 22 to flow through permeable element 12 and into sample chamber 36. The fluid will then move by reason of its pressure from the sample chamber 36 through sampling nipple 42 and thence through the sampling conduits to Ph meter 58 from whence it will be exhausted through conduit 59. The caustic content of this liquid will be determined by the Ph meter and the result translated into an electrical signal which may be used to determine the amount of caustic imput from source 24 by known apparatus (not shown). If desired, fluid may be exhausted from chamber 36 directly through conduit 51 by operation of valve 50 or through conduit 59 by operation of valve 60.

It should be noticed from the foregoing description that with the conduit-facing surface of permeable element 12 substantially coextensive with the normal inner surface of the conduit, it will have much less wear than if it were otherwise positioned or configured and the material passing through the conduit will tend to clean the surface of the permeable element and prevent clogging of the fiber fraction of the pulp stock thereon.

It should further be noted that the compound nature of permeable member 12, with a minimum of orifices in the two elements completely coinciding, will tend to maintain more even pressure differential over the entire surface of the permeable element. A plate having holes used alone or a screen used alone do not operate as well or as efficiently as the compound permeable element of my invention.

It should further be noted that from the positioning of my sampler there will be little delay in sampling changes in caustic content of pulp stock passing thereby and this information may be used to regulate that caustic content without undue delay.

It should further be noted that my sampler may be readily used in presently existing facilities in the present day paper manufacturing processes without any substantial changes therein.

The foregoing description of my invention is necessarily of a detailed nature so that a specific embodiment of it might be set forth as required, but it is to be understood that various modifications of detail, rearrangement and multiplication of parts may be resorted to without departing from its spirit, essence or scope.

Having thusly described my invention, what I desire to protect by Leters Patent and, what I claim is:

1. Apparatus for withdrawing a sample of the liquid fraction of paper pulp stock from the periphery of a conduit carrying such stock under pressure above the pressure of the ambient atmosphere comprising, in combination:
    a sampler having a peripherally defined extraction chamber carried externally of the conduit with a permeable member forming an interface between the interior member comprising
        a plate and screen joined at their edges by a rigid frame substantially the same size and configuration as the interface and the thickness of the screen and the plate being substantially the same as the thickness of the conduit wall, and wherein the frame containing the permeable member is sealed to the conduit and sampler so that the outer surface of the screen is coincident with the inner surface of the conduit;
    valve means for adjustably regulating the pressure in the sampler chamber between that of the pulp stock and that of the ambient atmosphere; and
    conduit means for removing the liquid fraction in the sampler chamber for subsequent testing.

* * * * *